US007812156B2

(12) United States Patent
Jackson et al.

(10) Patent No.: US 7,812,156 B2
(45) Date of Patent: Oct. 12, 2010

(54) OPTICAL BRIGHTENING AGENTS

(75) Inventors: Andrew Clive Jackson, Harrogate (GB); Nicholas Philip Lock, Bradford (GB)

(73) Assignee: Clariant Finance (BVI) Limited, Tortola (VG)

( * ) Notice: Subject to any disclaimer, the term of this patent is extended or adjusted under 35 U.S.C. 154(b) by 630 days.

(21) Appl. No.: 11/630,424

(22) PCT Filed: Jun. 24, 2005

(86) PCT No.: PCT/EP2005/052960

§ 371 (c)(1),
(2), (4) Date: Dec. 22, 2006

(87) PCT Pub. No.: WO2006/000573

PCT Pub. Date: Jan. 5, 2006

(65) Prior Publication Data

US 2007/0245503 A1    Oct. 25, 2007

(30) Foreign Application Priority Data

Jun. 28, 2004    (EP)    .................... 04015099

(51) Int. Cl.
C09B 23/00    (2006.01)
D06L 3/12    (2006.01)
(52) U.S. Cl. .................. 544/193.2; 544/194; 8/442; 8/648
(58) Field of Classification Search ........ 8/442; 544/193.2
See application file for complete search history.

(56) References Cited

U.S. PATENT DOCUMENTS

| 5,873,913 | A | * | 2/1999 | Cowman et al. ............ 8/648 |
| 6,890,454 | B2 | | 5/2005 | Farrar et al. |
| 7,019,134 | B2 | | 3/2006 | Farrar et al. |
| 7,198,731 | B2 | | 4/2007 | Jackson |

FOREIGN PATENT DOCUMENTS

| CH | 532686 | | 1/1973 |
| JP | 52078235 A | * | 7/1977 |
| JP | 62106965 | | 5/1987 |
| WO | WO 96/00221 | | 1/1996 |
| WO | WO 98/42685 | | 10/1998 |
| WO | WO 99/42454 | | 8/1999 |
| WO | WO 02/055646 | | 7/2002 |
| WO | WO 03/044275 | | 5/2003 |
| WO | WO 03044275 A1 | * | 5/2003 |

OTHER PUBLICATIONS

Derwent Abstract Acc. No. 1977-56793Y, english abstract for JP 52-078235.*
International Search Report for PCT/EP2005/052960 mailed Sep. 13, 2005.
PCT Written Opinion of the International Searching Authority for PCT/EP2005/052960, mailed Sep. 13, 2005.
PCT Notification of Transmittal of the International Preliminary Examination Report for PCT/EP2005/052960, mailed Aug. 22, 2006.
Claussen et al., "Ways to deactivate light-induced excited states of additives in polymers Structure-activity relationship in a group of stilbene-triazine optical brightening agents. Preliminary results ways to deactivate light-induced excited states of additives in polymers"—Bundesminist. Forsch Technol., Weltraum forsch. Weltrantechnol BMPT-FB-W 81-046 pp. 1-35; XP009048592 Dec. 1981.
Wilkowska et al., "Structure-Activity relationship in a group of stilbene-triazine optical brightening agents, Preliminary results," Organika Volume Date 1999-2000; pp. 85-94; 2001.
Machine Assisted English Translation of JP 52-78235 published Jul. 1, 1997.
English Abstract for JP 621069565, published May 18, 1987.
English Abstract for CH 532686, published Jan. 15, 1973.

* cited by examiner

*Primary Examiner*—Harold Y Pyon
*Assistant Examiner*—Katie Hammer
(74) *Attorney, Agent, or Firm*—Anthony A. Bisulca (57) ABSTRACT

The instant invention relates to stilbene optical brightening agents which combine a high solubility in water while providing superior fluorescent whitening effects when applied to the surface of paper in either the size-press or in a pigmented coating composition and which show a reduced anionic charge. The instant optical brighteners may also be used for finishing of textiles.

4 Claims, 2 Drawing Sheets

OPTICAL BRIGHTENING AGENTS

The instant invention relates to stilbene optical brightening agents which combine a high solubility in water while providing superior fluorescent whitening effects when applied to the surface of paper in either the size-press or in a pigmented coating composition and which show a reduced anionic charge.

PRIOR ART

Stilbene optical brightening agents (OBAS) of the following formula in which
M is typically an alkali metal atom,
n is 0, 1, or 2, and
R is an amino acid residue from which a hydrogen atom of the amino group has been removed, such as have been disclosed in, e.g. Japanese Kokai 62-106965, PCT Application WO 96/00221 and PCT Application WO 98/42685, represent the state-of-the-art for producing coated papers with a high degree of whiteness.

Compounds of said formula typically have good solubility in water which is advantageous for the paper industry in which optical brighteners are most conveniently marketed and used in the form of aqueous solutions.

The high anionic charge generated by the amino acid residues can however create a difficulty for papermakers who wish to recycle broke—that is, to repulp any paper waste generated in the paper making process—in that the optical brightener can be extracted in the repulping process leading to a build-up of anionic charge in the system which can interfere with cationic chemicals used, e.g. for sizing, or retention and drainage purposes.

There is therefore a need for optical brighteners which combine the high solubility in water characteristic of said compounds with a reduced anionic charge.

DESCRIPTION OF THE INVENTION

Surprisingly, we have found that compounds of formula (1) combine a reduced anionic charge with a high solubility in water while providing superior fluorescent whitening effects when applied to the surface of paper in either the size-press or in a pigmented coating composition.

The present invention provides a compound of formula (1)

(1)

in which

M is hydrogen, an alkali metal cation, ammonium or ammonium which is mono-, di- or trisubstituted by a $C_2$-$C_3$-hydroxyalkyl radical, n is 0, 1, or 2,

$R^1$ is hydrogen, a straight-chain $C_1$-$C_8$ alkyl or branched $C_3$-$C_8$ alkyl group which is not substituted by a heteroatom, and $R^2$ and $R^3$ are each, independently of one another, a straight-chain $C_1$-$C_8$ alkyl or branched $C_3$-$C_8$ alkyl group which is not substituted by a heteroatom, and does not form a ring, or mixtures of said compounds.

Further objects of the instant invention are a process for the preparation of compounds of formula (1), and the use of compounds of formula (1) as optical brightening agents, especially for paper.

The compounds of formula (1) are prepared by stepwise reaction of a cyanuric halide with a) a diamine of formula (2)

b) an amine of formula (3)

and c) an amine of formula (4)

As a cyanuric halide there may be employed the fluoride, chloride or bromide. Cyanuric chloride is preferred.

Each reaction may be carried out in an aqueous medium, the cyanuric halide being suspended in water, or in an aqueous/organic medium, the cyanuric halide being dissolved in a solvent such as acetone. Each amine may be introduced without dilution, or in the form of an aqueous solution or suspension. The amines can be reacted in any order, although it is preferred to react the aromatic amines first. Each amine may be reacted stoichiometrically, or in excess. Typically, the aromatic amines are reacted stoichiometrically, or in slight excess; the aliphatic amines are generally employed in an excess of 5-30% over stoichiometry.

For substitution of the first halogen of the cyanuric halide, it is preferred to operate at a temperature in the range of 0 to 20° C., and under acidic to neutral pH conditions, preferably in the pH range of 2 to 7. For substitution of the second halogen of the cyanuric halide, it is preferred to operate at a temperature in the range of 20 to 60° C., and under weakly acidic to weakly alkaline conditions, preferably at a pH in the range of 4 to 8. For substitution of the third halogen of the cyanuric halide, it is preferred to operate at a temperature in the range of 60 to 102° C., and under weakly acidic to alkaline conditions, preferably at a pH in the range of 7 to 10. The pH may be controlled by addition of suitable acids or bases as necessary, preferred acids being e.g., hydrochloric acid, sulphuric acid, formic acid or acetic acid, preferred bases being e.g., alkali metal (e.g., lithium, sodium or potassium) hydroxides, carbonates or bicarbonates, or aliphatic tertiary amines e.g. triethanolamine or triisopropanolamine. The aromatic amines of formula (3) are exemplified by aniline, aniline-2-sulphonic acid, aniline-3-sulphonic acid, aniline-4-sulphonic acid, aniline-2,4-disulphonic acid and aniline-2,5-disulphonic acid. Preferably, (3) is aniline-2,5-disulphonic acid.

The aliphatic amines of formula (4) are exemplified by isopropylamine, N-methylisopropylamine, N-ethylisopropylamine, 2-butylamine, 2-amino-3-methylbutylamine, 1-ethylpropylamine, 1,3-dimethylbutylamine and 1,5-dimethylhexylamine. Preferably (4) is isopropylamine, N-methylisopropylamine or 2-butylamine.

The optical brightening agents of the invention have the advantage of lower anionic charge compared to analogous compounds of the prior art. Surprisingly, such optical brightening agents also have higher solubility in water than analogous compounds in which the aliphatic amine either has only one alkyl substituent on an α-carbon, or is substituted by a hydroxyl group. Aliphatic amines of the former type are exemplified by diethylamine as described in Swiss Patent CH 532,686. Aliphatic amines of the latter type are exemplified by 2-amino-1-propanol as described by Wilkowska and Konopski in *Organika*, 2001, volume 1999-2000, pages 85-94.

The synthesized compounds of formula (1) may, if desired, be separated and isolated in a conventional way, e.g. by salting out or by precipitation by addition of an acid, and then filtered, washed and dried. If desired, the solution of the synthesized compound may be desalinated and optionally concentrated, e.g. by ultrafiltration or membrane filtration. Alternatively, the filtered, washed and optionally dried compound may also be redissolved in water and the solution so-formed may be desalinated and optionally concentrated.

The desalinated aqueous solution of the compound may, if desired, be dried. The liquid or dry compounds may be used as such or may, if desired, by blended with conventional blending agents, such as solubilizing aids or hydrotropes, e.g. urea or mono-, di- or triethanolamine, or other additives such as polyethyleneglycols or polyvinylalcohols. In a preferred aspect to the invention, the compounds of formula (1) are used in the form of an aqueous concentrated solution, e.g. at a concentration of 5 to 55, preferably 10 to 40% by weight. In a further preferred aspect to the invention, the aqueous concentrated solutions of compounds of formula (1) contain 2 to 40, preferably 5 to 20% by weight polyethyleneglycol.

The compounds of formula (1) are suitable for use as optical brightening agents, particularly for the optical brightening of cellulosic substrates, e.g. textiles, non-wovens or paper.

For the optical brightening of textiles and non-wovens, the compounds of formula (1) may, for example, be employed in padding processes, where the brightener concentration in the treatment bath may be kept almost constant. In the finishing of textiles (fabrics or, preferably, non-woven fabrics) with binding agents, especially synthetic resins, the optical brightener may be added to the synthetic resin either in the treatment bath or before. The brightener may be fixed, and the finishing agent cross-linked, in accordance with the cold dwell process or by heat treatment, optionally after intermediate drying. Owing to their stability towards acids and salts, e.g. magnesium chloride and zinc chloride, the compounds of formula (1) are also suitable for the optical brightening and simultaneous crease-proof finish of cotton. They may be employed at concentrations in the range of 0.01 to 2.5, preferably 0.03 to 1.0% optical brightener based on dry substrate.

The compounds of formula (1) are particularly suitable as optical brightening agents for the brightening of paper and non-wovens, more particularly they are preferred for optical brightening of paper after sheet formation, or non-wovens after web formation.

Most preferably, the compounds of formula (1) are suitable for the brightening of paper after sheet formation. This may be effected by adding the optical brightener to a pigmented coating composition, or to a sizing solution or suspension. The paper may be of fine or coarse nature, and of bleached or unbleached cellulose.

For the treatment of paper in the size-press, sizing solutions or suspensions containing 0.2 to 30, preferably 1 to 15 grams per litre of the optical brightener, may be used. The sizing solution or suspension also contains a binding agent in a concentration of preferably 2 to 15% by weight. The pH is typically in the range 5-9, preferably 6-8.

The binding agent or size is typically an enzymatically or chemically modified starch, e.g. oxidized starch, hydroxyethylated starch or acetylated starch.

Pigmented coating compositions are essentially aqueous compositions that contain at least one binder and a white pigment, in particular an opacifying white pigment, and may additionally contain further additives such as dispersing agents and defoamers.

Although it is possible to produce coating compositions that are free from white pigments, the best white substrates for printing are made using opaque coating compositions that contain 10-70% white pigment by weight. Such white pigments are generally inorganic pigments, e.g., aluminium silicates (kaolin, otherwise known as china clay), calcium carbonate (chalk), titanium dioxide, aluminium hydroxide, barium carbonate, barium sulphate, or calcium sulphate (gypsum).

The binders may be any of those commonly used in the paper industry for the production of coating compositions and may consist of a single binder or of a mixture of primary and secondary binders. The sole or primary binder is preferably a synthetic latex, typically a styrene-butadiene, vinyl acetate, styrene acrylic, vinyl acrylic or ethylene vinyl acetate polymer. The secondary binder may be, e.g., starch, carboxymethylcellulose, casein, soy polymers, or polyvinyl alcohol.

The sole or primary binder is used in an amount typically in the range 5-25% by weight of white pigment. The secondary binder is used in an amount typically in the range 0.1-2% by weight of white pigment; starch however is typically used in the range 5-10% by weight of white pigment.

The optical brightener of formula (1) is used in an amount typically in the range 0.01-1% by weight of white pigment, preferably in the range 0.05-0.5% by weight of white pigment.

The following examples shall explain the instant invention in more details. If not indicated otherwise, "%" and "parts" are meant by weight.

EXAMPLES

Preparative Example 1

A solution of 26.6 parts aniline-2,5-disulphonic acid and 8.4 parts sodium hydroxide in 40 parts water is added to a stirred suspension of 19.4 parts cyanuric chloride in 60 parts ice water. The pH is kept at 6 by the dropwise addition of 30% sodium hydroxide. The mixture is stirred below 10° C. until primary aromatic amine groups can no longer be detected by the diazo reaction. A solution of 18.5 parts 4,4'-diaminostilbene-2,2'-disulphonic acid and 4.0 parts sodium hydroxide in 25 parts water is then added, the pH is adjusted to between 6.5 and 7.5 by the addition of 30% sodium hydroxide and the mixture is stirred at 30° C. until a negative diazo reaction is obtained. 8.4 parts 2-butylamine are added, and the mixture is heated at reflux for 2 hours, the pH being kept at 8 to 9 by the addition of 30% sodium hydroxide. The product is diluted to 400 parts with water to give an aqueous solution comprising 16.3% of (5) as its hexasodium salt and 4.4% sodium chloride.

(5)

Preparative Example 2

A solution of 26.6 parts aniline-2,5-disulphonic acid and 8.4 parts sodium hydroxide in 40 parts water is added to a stirred suspension of 19.4 parts cyanuric chloride in 60 parts ice water. The pH is kept at 6 by the dropwise addition of 30% sodium hydroxide. The mixture is stirred below 10° C. until primary aromatic amine groups can no longer be detected by the diazo reaction. A solution of 18.5 parts 4,4'-diaminostilbene-2,2'-disulphonic acid and 4.0 parts sodium hydroxide in 25 parts water is then added, the pH is adjusted to between 6.5 and 7.5 by the addition of 30% sodium hydroxide and the mixture is stirred at 30° C. until a negative diazo reaction is obtained. 8.4 parts 2-butylamine are added, and the mixture is heated at reflux for 2 hours, the pH being kept at 8 to 9 by the addition of 30% sodium hydroxide. The aqueous solution so-formed is cooled to 80° C. and treated with 20 parts polyethylene glycol of average molecular weight 1,500. The solution is returned to reflux for 10 minutes, then diluted to 400 parts with water. The resulting aqueous solution, comprising 16.3% of (5) as its hexasodium salt, 5% polyethylene glycol 1,500 and 4.4% sodium chloride, has an anionic charge of 0.75 μeq/g (Lasertrim particle charge analyzer), and shows no signs of precipitation after 2 weeks at 5° C.

Comparative Example 2A

Preparative Example 2 is repeated using 15.3 parts iminodiacetic acid in place of 8.4 parts 2-butylamine to give an aqueous solution comprising 18.9% of (6) as its decasodium salt, 5% polyethylene glycol 1,500 and 4.4% sodium chloride. The solution has an anionic charge of 1.35 μeq/g (Lasertrim particle charge analyzer).

(6)

Comparative Example 2B

Preparative Example 2 is repeated using 8.4 parts diethylamine in place of 8.4 parts 2-butylamine to give an aqueous solution comprising 16.3% of (7) as its hexasodium salt, 5% polyethylene glycol 1,500 and 4.4% sodium chloride. The solution precipitates within 6 days at 5° C.

Preparative Example 3

Preparative Example 2 is repeated as far as completion of the reaction with 2-butylamine. The aqueous solution so-formed is desalinated by membrane filtration and concentrated to a solution containing up to 40% of (5) in the form of its hexasodium salt. The solution is warmed to 80° C. and (7)

Comparative Example 2C

Preparative Example 2 is repeated using 8.6 parts DL-2-amino-1-propanol in place of 8.4 parts 2-butylamine to give an aqueous solution comprising 16.4% of (8) as its hexasodium salt, 5% polyethylene glycol 1,500 and 4.4% sodium chloride. The solution precipitates within 6 days at 5° C.

treated with 10 parts polyethylene glycol of average molecular weight 1,500. The solution is returned to reflux for 10 minutes, then diluted to 200 parts with water. The resulting aqueous solution has a viscosity of 0.02-0.03 Pa·s at 20° C. and comprises 32.6% of (5) as its hexasodium salt, 5% polyethylene glycol 1,500 and 0.1% sodium chloride.

(8)

Preparative Example 4

Preparative Example 2 is repeated using 6.8 parts isopropylamine in place of 8.4 parts 2-butylamine to give an aqueous solution comprising 16.0% of (9) as its hexasodium salt, 5% polyethylene glycol 1,500 and 4.4% sodium chloride.

Preparative Example 6

Preparative Example 2 is repeated using 10.0 parts 1,2-dimethylpropylamine in place of 8.4 parts 2-butylamine to give an aqueous solution comprising 16.7% of (11) as its hexasodium salt, 5% polyethylene glycol 1,500 and 4.4% sodium chloride.

(9)

Preparative Example 5

Preparative Example 2 is repeated using 8.4 parts N-methylisopropylamine in place of 8.4 parts 2-butylamine to give an aqueous solution comprising 16.3% of (10) as its hexasodium salt, 5% polyethylene glycol 1,500 and 4.4% sodium chloride.

(10)

(11)

Preparative Example 7

Preparative Example 2 is repeated using 11.6 parts 1,3-dimethylbutylamine in place of 8.4 parts 2-butylamine to give an aqueous solution comprising 17.0% of (12) as its hexasodium salt, 5% polyethylene glycol 1,500 and 4.4% sodium chloride.

(12)

Preparative Example 8

Preparative Example 2 is repeated using 14.9 parts 1,5-dimethylhexylamine in place of 8.4 parts 2-butylamine to give an aqueous solution comprising 17.7% of (13) as its hexasodium salt, 5% polyethylene glycol 1,500 and 4.4% sodium chloride.

(13)

Preparative Example 9

A solution of 18.2 parts aniline-4-sulphonic acid and 4.2 parts sodium hydroxide in 20 parts water is added to a stirred suspension of 19.4 parts cyanuric chloride in 60 parts ice water. The pH is kept at 6 by the dropwise addition of 30% sodium hydroxide. The mixture is stirred below 10° C. until primary aromatic amine groups can no longer be detected by the diazo reaction. A solution of 18.5 parts 4,4'-diaminostilbene-2,2'-disulphonic acid and 4.0 parts sodium hydroxide in 25 parts water is then added, the pH is adjusted to between 6.5 and 7.5 by the addition of 30% sodium hydroxide and the mixture is stirred at 30° C. until a negative diazo reaction is obtained. 8.4 parts 2-butylamine are added, and the mixture is heated at reflux for 2 hours, the pH being kept at 8 to 9 by the addition of 30% sodium hydroxide. The aqueous solution so-formed is cooled to 80° C. and treated with 20 parts polyethylene glycol of average molecular weight 1,500 and 80 parts urea. The solution is returned to reflux for 10 minutes, then diluted to 400 parts with water. The resulting aqueous solution comprises 13.8% of (14) as its tetrasodium salt, 5% polyethylene glycol 1,500, 20% urea and 4.4% sodium chloride.

(14)

Application Example 1

Sizing solutions are prepared by adding a solution of brightener (5) in the form of its sodium salt, made as described in Preparative Example 2, at a range of concentrations from 10 to 80 g/l to a stirred, aqueous solution of an anionic potato starch (Perfectamyl A4692 from AVEBE B.A.) at 60° C. The solution is diluted with water to a starch content of 5% and allowed to cool.

The sizing solution is poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier. The dried paper is allowed to condition, then measured for CIE whiteness on a calibrated Elrepho spectrophotometer. The measured values show a surprisingly high level of whiteness.

| OBA Concentration (g/l) | CIE Whiteness using Brightener of Example 2 |
| --- | --- |
| 0 | 95.5 |
| 10 | 108.7 |
| 20 | 115.0 |
| 40 | 122.9 |
| 60 | 126.9 |
| 80 | 129.1 |

Figure 1:
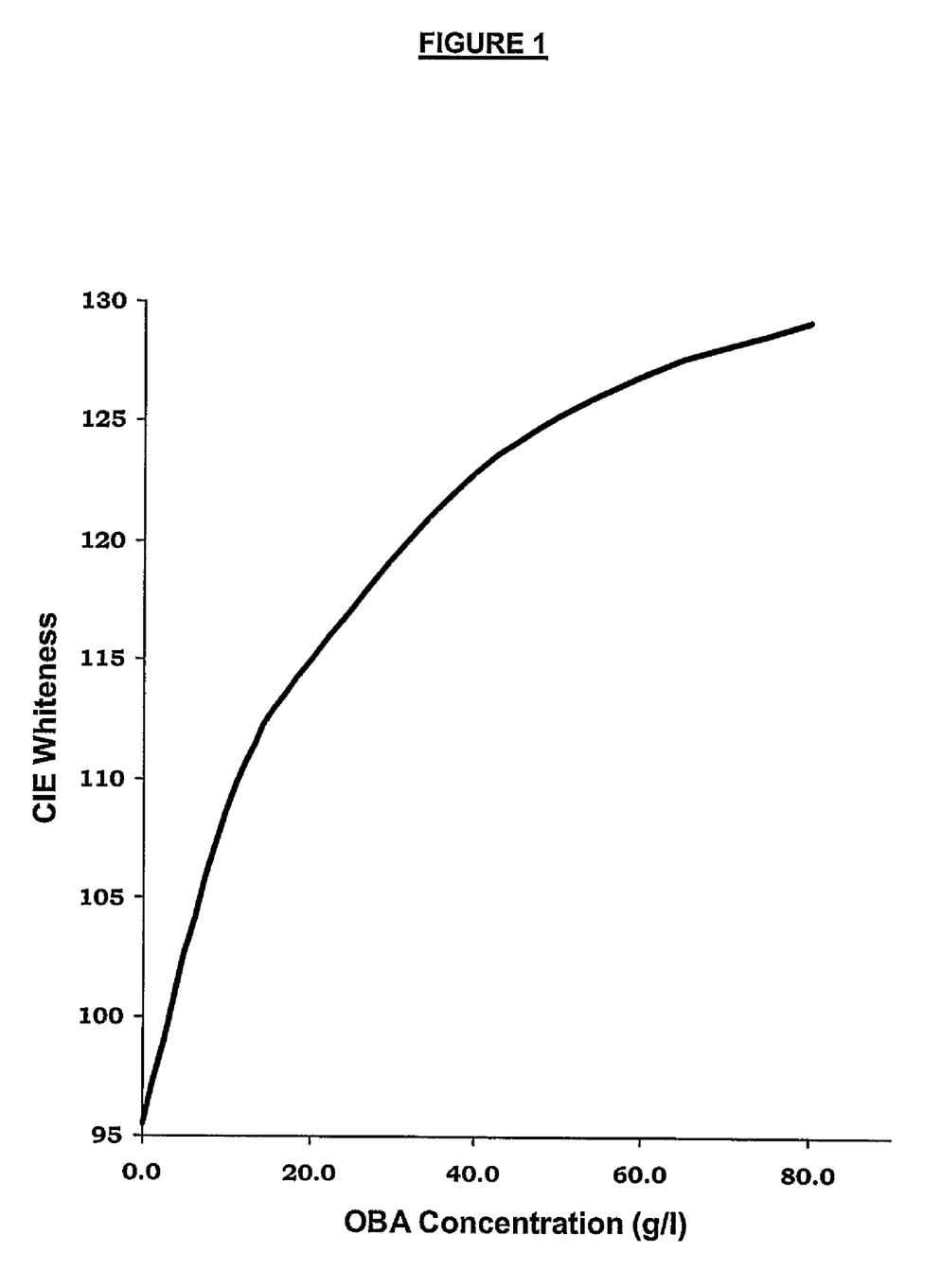
FIG. 1 is a graphical representation of the results of Application Example 1.

The results are also shown in graphical form in FIG. 1.

Application Example 2

A coating composition is prepared containing 500 parts chalk (commercially available under the trade name Hydrocarb 90 from OMYA), 500 parts clay (commercially available under the trade name Kaolin SPS from IMERYS), 470 parts water, 6 parts dispersing agent (a sodium salt of a polyacrylic acid commercially available under the trade name Polysalz S from BASF), 200 parts latex (an acrylic ester copolymer commercially available under the trade name Acronal S320D from BASF) and 400 parts of a 20% solution of Anionic Oxidized Potato Starch (commercially available under the trade name Perfectamyl A4692 from AVEBE) in water. The solids content is adjusted to 65% by the addition of water, and the pH is adjusted to 8-9 with sodium hydroxide.

The solution of brightener (5) in the form of its sodium salt, made as described in Preparative Example 2, is added at a range of concentrations from 0.1 to 0.6% to the stirred coating composition. The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. The dried paper is allowed to condition, then measured for CIE Whiteness on a calibrated Elrepho spectrophotometer.

| OBA Concentration (%) | CIE Whiteness using Brightener of Example 2 |
| --- | --- |
| 0 | 88.3 |
| 0.4 | 96.6 |
| 0.8 | 101.1 |
| 1.2 | 105.2 |
| 1.6 | 107.8 |
| 2.0 | 110.7 |
| 3.0 | 115.3 |

Figure 2:
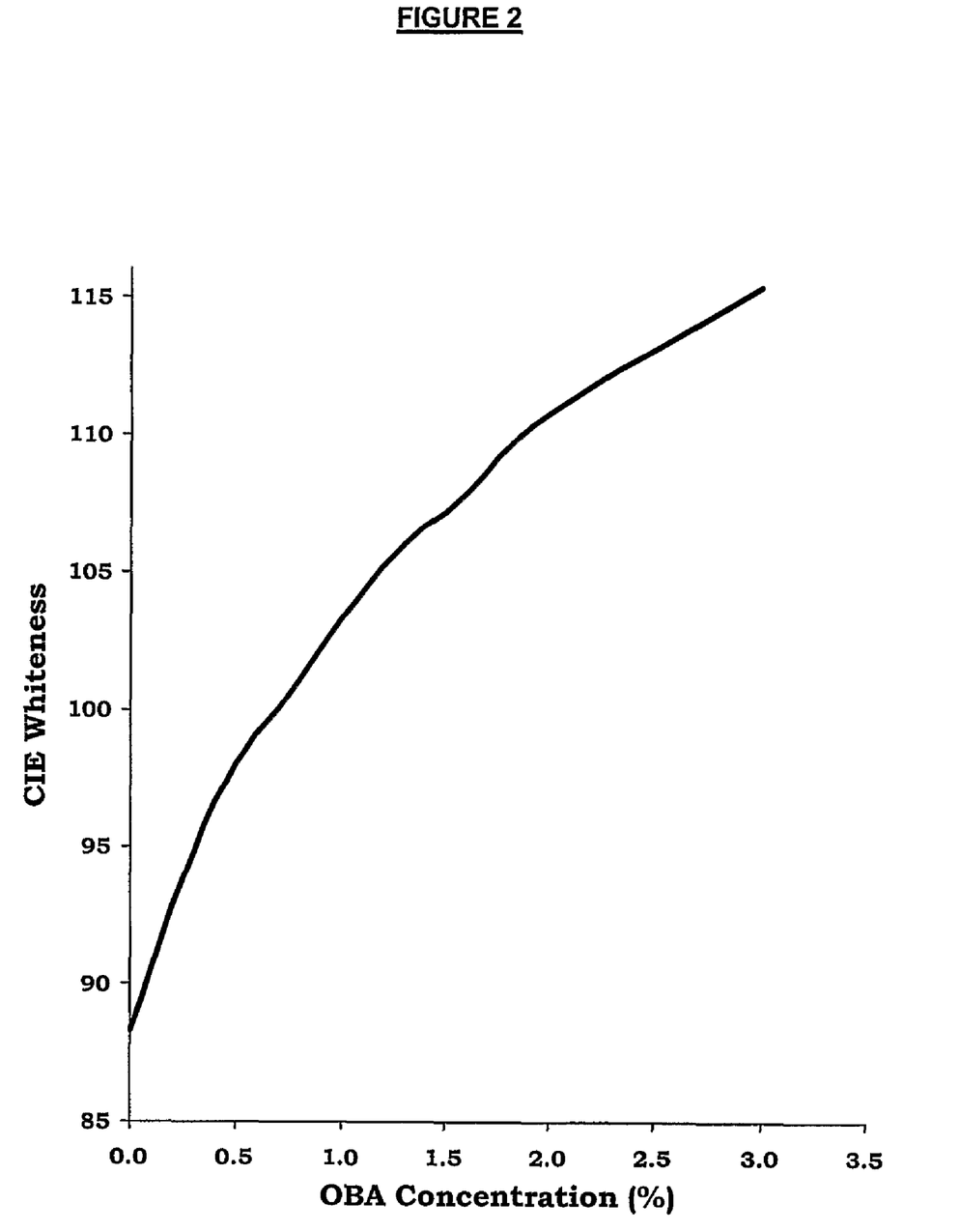
FIG. 2 is a graphical representation of the results of Application Example 2.

The results are also shown in graphical form in FIG. 2.

The invention claimed is:

1. A compound of formula (I)

$$\text{(I)}$$

wherein

M is hydrogen, an alkali metal cation, ammonium or ammonium which is mono-, di- or trisubstituted by a $C_2$-$C_3$-hydroxyalkyl radical, n is 1 or 2, $R^1$ is hydrogen, a straight-chain $C_1$-$C_8$ alkyl or branched $C_3$-$C_8$ alkyl group which is not substituted by a heteroatom, and $R^2$ and $R^3$ are each, independently of one another, a straight-chain $C_1$-$C_8$ alkyl or branched $C_3$-$C_8$ alkyl group which is not substituted by a heteroatom, and does not form a ring.

2. A compound according to claim 1 wherein

M is hydrogen, an alkali metal cation or ammonium, n is 1 or 2, $R^1$ is hydrogen, a straight-chain $C_1$-$C_4$ alkyl or branched $C_3$-$C_5$ alkyl group which is not be substituted by a heteroatom, and $R^2$ and $R^3$ are each, independently of one another, a straight-chain $C_1$-$C_4$ alkyl or branched $C_3$-$C_6$ alkyl group which is not substituted by a heteroatom, and does not form a ring.

3. A compound according to claim 2 wherein

M is hydrogen, sodium or potassium, n is 1 or 2, $R^1$ is hydrogen, methyl, ethyl, propyl or i-propyl, and $R^2$ and $R^3$ are each, independently of one another, methyl, ethyl or propyl, or i-propyl, i-butyl, i-pentyl or i-hexyl.

4. A compound according to claim 3 wherein

M is hydrogen or sodium, n is 1 or 2, $R^1$ is hydrogen or methyl, and $R^2$ and $R^3$ are each, independently of one another, methyl or ethyl.

* * * * *